US007582283B2

(12) United States Patent
Taylor et al.

(10) Patent No.: US 7,582,283 B2
(45) Date of Patent: Sep. 1, 2009

(54) CONTRAST AGENTS TO IMPROVE GASTROINTESTINAL TRACT OPACIFICATION DURING ABDOMINAL AND PELVIC CT SCANS

(75) Inventors: Andrew J. Taylor, Madison, WI (US); Jeffrey J. Hebert, Madison, WI (US); Thomas C. Winter, III, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 820 days.

(21) Appl. No.: 10/794,043

(22) Filed: Mar. 5, 2004

(65) Prior Publication Data

US 2005/0180921 A1 Aug. 18, 2005

Related U.S. Application Data

(60) Provisional application No. 60/544,956, filed on Feb. 13, 2004.

(51) Int. Cl.
*A61K 49/04* (2006.01)
*A61B 5/05* (2006.01)

(52) U.S. Cl. .................... 424/9.4; 424/9.41; 424/9.411; 424/9.45; 424/9.451; 600/425

(58) Field of Classification Search ............. 424/9.411, 424/9.41, 9.4; 382/131
See application file for complete search history.

(56) References Cited

U.S. PATENT DOCUMENTS 2,996,433 A * 8/1961 Hoppe et al. ............. 424/9.411
5,782,762 A * 7/1998 Vining ........................ 600/407
2004/0241093 A1* 12/2004 Lauenstein et al. ........... 424/9.3

OTHER PUBLICATIONS

Fletcher, Radiology, 2000, 216, p. 704-711.*
Pineau et al., Gastrointestinal Oncology, 1999, 116 (Supp.), p. A485.*
Catalanom, Radiol. Med., 1995, 89(6), pp. 798-803 (abstract).*
Laghi, A. et al., Polyethylene glycol solution as an oral contrast agent for MR imaging of the small bowel, Acad. Radiology, Aug. 2002. 9 Suppl 2:S355-6.

* cited by examiner

*Primary Examiner*—Michael G Hartley
*Assistant Examiner*—Leah Schlientz
(74) *Attorney, Agent, or Firm*—Whyte Hirschboeck Dudek, S.C.

(57) ABSTRACT

Methods of imaging a portion of a body of a patient are provided. In the methods, a contrast agent including an iso-osmotic contrast agent is administered to the patient. In a preferred embodiment, the iso-osmotic contrast agent comprises polyethylene glycol (PEG) and electrolytes, which make the PEG iso-osmotic. In a preferred embodiment, a positive contrast agent, such as an iodine-based contrast agent, is added to the PEG. The iso-osmotic contrast agent can be administered in volumes that are lower than previous contrast agents. The iso-osmotic contrast agent can be administered in combination with a positive intravenous contrast agent. At least one image of the portion of the patient's body is obtained, such as by computed tomography, after the contrast agent is administered. The methods can be used to image a pelvis, GI tract, and/or appendix of the patient. Iso-osmotic contrast agents are also provided.

16 Claims, 4 Drawing Sheets

CONTRAST AGENTS TO IMPROVE GASTROINTESTINAL TRACT OPACIFICATION DURING ABDOMINAL AND PELVIC CT SCANS

CROSS-REFERENCE TO RELATED APPLICATION

This application claims priority from U.S. Provisional patent application Ser. No. 60/544,956, filed on Feb. 13, 2004, entitled "Contrast Agents to Improve Gastrointestinal Tract Opacification During Abdominal and Pelvic CT Scans", the entirety of which is incorporated herein by reference.

BIBLIOGRAPHY

Complete bibliographic citations of the references referred to herein by reference numbers in parentheses can be found below in the Bibliography section.

FIELD OF THE INVENTION

The invention relates to compositions and methods for their use during visualization of the gastrointestinal tract during computed tomography (CT) scans.

DESCRIPTION OF THE RELATED ART

Computed tomography (CT)—sometimes called "CAT scan" or "CT scan"—uses special x-ray equipment to obtain image data from different angles around the body, then uses computer processing of the information to generate a cross-sectional image of body tissues and organs.

CT imaging is particularly useful because it can show several types of tissue with great clarity, including organs such as the liver, spleen, pancreas and kidneys. Using specialized equipment and expertise to create and interpret CT scans of the gastrointestinal tract including the stomach, small bowel, and large bowel, an experienced radiologist can accurately diagnose many causes of abdominal pain, such as an abscess in the abdomen, inflamed colon or colon cancer, diverticulitis, and appendicitis. Often, no additional diagnostic work-up is necessary, and treatment planning can begin immediately. CT of the body is a patient-friendly exam that involves acceptable diagnostic radiation exposure.

Because it is a non-invasive procedure that provides detailed, cross-sectional images of all types of tissue, CT is becoming the preferred method for diagnosing many diseases of the bowel and colon, including diverticulitis, bowel obstruction, bowel ischemia, bowel inflammation and appendicitis, as well as for visualizing the liver, spleen, pancreas and kidneys. In cases of acute abdominal distress, CT can quickly identify the source of pain. Especially when pain is caused by infection and inflammation, the speed, ease and accuracy of a CT examination can reduce the risk of serious complications caused by a perforated appendix or ruptured diverticulum and the subsequent spread of infection.

CT also is often the preferred method for diagnosing many different cancers, including colon cancer, since the image allows a physician to confirm the presence of local or distant tumor spread. CT examinations of the lower GI tract can be used to plan and properly administer radiation treatments for tumors, and to guide biopsies and other minimally invasive procedures. Many dedicated shock-trauma centers have a CT scanner in the trauma department. CT can also play a significant role in the detection, diagnosis and treatment of vascular disorders that can lead to stroke, gangrene or kidney failure.

In many ways, CT scanning works very much like other x-ray examinations. In CT scanning, small, controlled amounts of x-ray radiation are passed through the patient's body, while different tissues absorb the radiation at different rates. With plain radiology, i.e., a traditional x-ray, an image of the inside of the body is captured when special film is exposed to the absorbed x-rays. With CT, the film is replaced by an array of detectors, which measure the x-ray profile.

Inside the CT scanner is a rotating gantry that has an x-ray tube mounted on one side and an arc-shaped detector mounted on the opposite side. The tube generates a fan-shaped beam that is received by the detector. The gantry is then rotated about the patient's body. A technologist begins by positioning the patient on the CT table. The patient's body may be supported by pillows to help hold it still and in the proper position during the scan. During each full rotation of the gantry, as the fan-shaped x-ray beam passes through the patient's body, an image of a thin section of the patient's body is acquired. The detector records about 1,000 images—or profiles—of the expanded x-ray beam with each rotation. As the study proceeds, the patient and table move slowly into the CT scanner. Depending on the area of the body being examined, the increments of movement may be so small that they are almost undetectable, or large enough that the patient feels the sensation of motion. The resulting scan is typically referred to as "spiral CT." The profiles are then reconstructed by a computer into two-dimensional or three-dimensional images of the scanned sections. Multiple computers are typically used to control the entire CT system. CT scanning causes no pain, and with spiral CT, the need for the patient to lie still for any length of time is reduced.

For examinations of the abdomen and lower gastrointestinal tract, patients may be asked to drink water or a positive contrast agent (also referred to as a contrast material or a contrast medium), a liquid that allows the radiologist to better see the stomach, small bowel and colon. Orally administered high density contrast materials have been used for opacification of bowel loops during abdominal-pelvic CT scans both for delineating bowel loops from adjacent structures, as well as for examining the bowel itself. However, with the development of CT angiographic (CTA) techniques that employ maximal intensity projection type image processing algorithms to display vascular structures in off-axial planes, the high attenuation bowel contrast agents create difficulties. Additionally, with the improved resolution of CT in general, the need for a high-attenuation contrast material has also significantly been reduced. Many investigators have evaluated low-density preparations as alternate oral contrast materials for abdominal-pelvic CT (1-6). Particular attention has been made to water and milk. Both of these are of low attenuation, but they have their own inherent problems. Specifically, water is rapidly absorbed in the stomach and small bowel, which limits its effectiveness in dilating the distal small bowel. Milk may not be well suited for patients in the large volumes needed for adequate small bowel distension.

Presently, water is used for all CT scans specifically designed to evaluate the abdominal vasculature. This includes pre-transplant CT scans for both liver transplant recipients and renal transplant donors. Water is also used for all CT scans designed to evaluate for certain liver cancers and for pancreatic abnormalities. Water is used to obtain some distension of the bowel in order to differentiate bowel from other anatomy or pathology. However, as stated above, the small bowel distally remains non-distended. This limits the diagnostic quality of the study to evaluate for bowel wall pathology.

Additionally, CT scans have been used for imaging patients suspected of having appendicitis. There has been much debate, but no consensus, as to the optimal CT technique for imaging such patients. Critical components of CT imaging in this patient population involve the best depiction of the appendix/periappendiceal area combined with an acceptable response time to acquire a diagnostic exam. The periappendiceal area is visualized to best advantage when the terminal ileum and at least the cecal portion of the colon are opacified, especially in the thin patient.

Where previous contrast agents were used, there has been frustration with the length of time between the request for an appendicitis CT and the adequate oral preparation of the patient to opacify the terminal ileum and cecum.

Therefore, what are needed are contrast agents for CT that both are low attenuation (similar to water or lower) and that adequately distend the small bowel throughout substantially its entirety. What are also needed are methods for using the contrast agents. In addition, what are needed are contrast agents for CT that consistently and rapidly opacify the terminal ileum and cecum in at least patients suspected of having appendicitis.

SUMMARY

The invention, which is defined by the claims set out at the end of this disclosure, is intended to solve at least some of the problems noted above. Methods of imaging a portion of a body of a patient are provided. In the methods, a contrast agent including an iso-osmotic agent is administered to the patient. At least one image of the portion of the patient's body is obtained after the contrast agent is administered. Preferably, the step of obtaining at least one image comprises obtaining a plurality of successive images by computed tomography, although other imaging techniques can be used. The methods can be used to image a pelvis, GI tract, and/or appendix of the patient.

In a preferred embodiment, the iso-osmotic contrast agent provided herein is administered to the patient as a solution containing about 65 g to about 500 g of polyethylene glycol dissolved in about 4000 cc of liquid. In a more preferred embodiment, the iso-osmotic contrast agent provided herein is administered to the patient as a solution containing about 236 g to about 420 g of polyethylene glycol dissolved in about 4000 cc of liquid.

The iso-osmotic contrast agents provided herein can be administered in smaller volumes than previous contrast agents. This reduces costs and improves patient satisfaction. In a preferred embodiment, the polyethylene glycol solution described above is administered to the patient in a 100 cc to 1500 cc volume. In another preferred embodiment, the polyethylene glycol solution described above is administered to the patient in a 250 cc to 1000 cc volume.

In a first preferred embodiment, the iso-osmotic contrast agent is orally administered without an orally administered positive contrast agent. The absence of an orally administered positive contrast agent improves visualization of some abnormalities within the GI tract due to the absence of the added illumination that a positive contrast agent would supply within the GI tract.

In a second preferred embodiment, the iso-osmotic contrast agent is orally administered with an orally administered positive contrast agent. The addition of an orally administered positive contrast agent improves visualization of some abnormalities within the GI tract due to the addition of the added illumination that a positive contrast agent supplies within the GI tract.

The iso-osmotic contrast agents can be administered in combination with a positive intravenous "IV" contrast agent, such as an iodine-based contrast agent. IV contrast agents allow visualization of blood vessels, as well as an improved visualization of such internal organs as the liver, pancreas, kidneys, spleen, and urinary bladder.

Also provided is a composition that includes an iso-osmotic agent and a positive contrast agent. The iso-osmotic contrast agent preferably comprises polyethylene glycol (PEG) and electrolytes, which make the PEG iso-osmotic. Using an iso-osmotic contrast agent beneficially provides a contrast agent that rapidly moves through the GI tract of the patient, even in the absence of peristalsis.

A preferred positive contrast agent is an iodine-based contrast agent or a barium-based contrast agent. Preferred iodine-based contrast agents include Gastrograffin™ and MD-Gastroview®.

BRIEF DESCRIPTION OF THE DRAWINGS

Preferred exemplary embodiments of the invention are illustrated in the accompanying drawings in which.

Figure 1A:
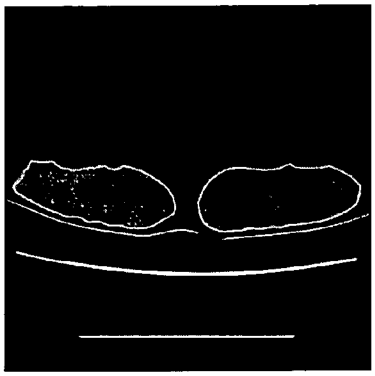
FIGS. 1A-1F show images from in vitro computed tomography (CT) exams that assess the attenuation values in Hounsfield Units (HU) of various contrast agents.

Before explaining embodiments of the invention in detail, it is to be understood that the invention is not limited in its application to the details of construction and the arrangement of the components set forth in the following description or illustrated in the drawings. The invention is capable of other embodiments or being practiced or carried out in various ways. Also, it is to be understood that the phraseology and terminology employed herein is for the purpose of description and should not be regarded as limiting.

DETAILED DESCRIPTION

A "contrast agent," as used herein, is any internally administered substance that has a different density or opacity from soft tissue on radiography or computed tomography (CT). For instance, water is a contrast agent because it has a different density than soft tissue on radiography or CT. Polyethylene glycol (PEG), which has the same density as water, also is a contrast agent. A positive contrast agent is one that appears white on CT. Positive contrast agents include, but are not limited to, barium-based and iodine-based contrast agents. Because water is not white, it is oftentimes referred to as a "negative contrast agent" even though it has a value of zero in Hounsfield Units. PEG can also be referred to as a negative contrast agent.

Contrast agents of the invention include those that are low attenuation and that adequately distend the small bowel throughout substantially its entirety. A preferred contrast agent has a similar or lower attenuation as water.

A preferred contrast agent is an iso-osmotic agent. Iso-osmotic agents beneficially move through the gastrointestinal (GI) tract in the absence of peristalsis, which is the process of involuntary wave-like successive muscular contractions by which food and other substances are moved through the digestive tract. This characteristic is particularly useful in patients in whom peristalsis ceases, including, but not limited to, those with inflammation of the peritoneum. In these patients, the iso-osmotic contrast agents move through the GI tract, whereas non iso-osmotic contrast agent may not.

Iso-osmotic agents are also advantageous in that they quickly move through the GI tract and quickly reach the colon. This characteristic beneficially decreases the time required to prepare a patient for CT. Previous contrast agents typically took up to two hours or more to reach the colon. In contrast, iso-osmotic contrast agents normally reach the colon within an hour. Thus, iso-osmotic contrast agents move a patient to a diagnosis more quickly than previous compositions. In an emergency room (ER), the time saved can decrease the cost of the ER, which typically costs about $800 per hour for overhead alone. Saving time can be particularly important with appendicitis, as the time saved can prevent an appendix from rupturing.

In summary, iso-osmotic agents are particularly useful in that they move through the GI tract in the absence of peristalsis. In addition, iso-osmotic agents move quickly through the GI tract, saving time and money.

In a first preferred embodiment, the iso-osmotic contrast agent is orally administered without an orally administered positive contrast agent. The absence of an orally administered positive contrast agent improves visualization of some abnormalities within the GI tract due to the absence of the added illumination that a positive contrast agent would supply within the GI tract.

In a second preferred embodiment, the iso-osmotic agent is orally administered with an oral positive contrast agent, such as a barium-based contrast agent or an iodine-based contrast agent. The inclusion of an oral positive contrast agent improves visualization of some abnormalities within the GI tract due to the added illumination supplied within the GI tract. Where a barium-based contrast agent is used, suspensory agents, such as gums or resins, are added to keep the barium in solution.

Preferred iodine-based contrast agents are diatrizoates (tri-iodinated, substituted benzene compounds), such as those sold under the trade names Gastrograffin™ and MD-Gastroview®. Gastrograffin™ and MD-Gastroview® can be administered, for example, in a preferred embodiment, by mixing it with an iso-osmotic agent. In a preferred embodiment, an iso-osmotic agent is added to an iodine-based contrast agent, such as Gastrograffin™, MD-Gastroview®, or any other suitable iodine-based contrast agent at a ratio of about 100:0.5 to about 100:3. In a more preferred embodiment, an iso-osmotic agent is added to an iodine-based contrast agent at a ratio of about 100:3. In a particularly preferred embodiment, 30 cc of Gastrograffin™ or MD-Gastroview® is added to 1000 cc of PEG and electrolytes, and the resulting solution is administered to a patient.

Where PEG and electrolytes are used as the iso-osmotic contrast agent, as is discussed immediately below, in a preferred embodiment, PEG at full strength is mixed with a positive contrast agent. In another preferred embodiment, ½ strength PEG is mixed with a positive contrast agent.

A preferred iso-osmotic agent is a mixture of PEG and electrolytes, the electrolytes being detailed below. Adding electrolytes to PEG results in an iso-osmotic solution. PEG is a low attenuation contrast agent that has an attenuation that is similar to water. PEG is also known as poly(oxyethylene) cetyl ether, poly(oxyethylene) palmityl ether, polyethylene oxide hexadecyl ether, polyethylene glycol cetyl ether, brij 38, brij 52, brij 56, brij W1, CA 16, atlas G 3802, atlas g 3816, BC 7, BC 10, BC 20, BC 20 tx, BC 30 tx, berol 28, cetocire, cetyl alcohol ethoxylate, nikkol BC 40, and numerous other trade names.

Unlike water, a PEG and electrolytes mixture is not absorbed in the stomach and small bowel. Therefore, unlike water, a PEG and electrolytes mixture distends the small bowel distally. As is detailed below in Example 1, a PEG and electrolytes mixture was found to distend the small bowel throughout its entirety. A PEG and electrolytes mixture also provides improved stomach distension. Distension of the small bowel and other segments of the GI tract are helpful because distension improves viewing of an abnormality within the distended structure. For example, if a small tumor exists in the bowel, it is much easier to visualize when the bowel is distended compared to when it is not distended.

Thus, a PEG and electrolytes mixture beneficially extends the small bowel and stomach better than water. The cost of a typical PEG and electrolytes mixture (currently about $6.75 to about $7.80/dose) exceeds that of water (negligible/dose). The cost of a typical PEG and electrolytes mixture also exceeds that of water/iodinated contrast (currently $1.75). However, the time saved and improved distension and thus visualization obtained with the PEG and electrolytes mixture far outweighs the elevated cost of PEG. In addition, the diagnosis and subsequent management of patients receiving the PEG-based contrast agents are more rapidly processed.

PEG and electrolytes mixtures can be purchased in powder form, e.g., under the trademarks GoLYTELY®, GoLyte®, Nulytely®, and Miralax. GoLYTELY® is sold as a mixture that includes 236 g PEG 3350 and electrolytes (22.74 g sodium sulfate (anhydrous), 6.74 g sodium bicarbonate, 5.86 g sodium chloride, and 2.97 g potassium chloride). Nulytely® is sold as a mixture that includes 420 g PEG 3350 and electrolytes (5.72 g sodium bicarbonate, 11.2 g sodium chloride, and 1.48 g potassium chloride).

In a preferred embodiment of the iso-osmotic contrast agent, PEG is combined with one or more electrolytes, such as one or more of sodium sulfate (anhydrous), sodium bicarbonate, sodium chloride, and potassium chloride, preferably in the respective ratios to PEG that are contained in GoLYTELY® or in Nulytely®.

PEG and electrolytes can be dissolved in water. Preferably, about 65 g to about 500 g of PEG and a respective ratio of electrolytes are dissolved in about 4000 cc of water. More preferably, about 236 g to about 420 g of PEG and a respective ratio of electrolytes are dissolved in about 4000 cc of water. The second range is based on the commercially available forms of PEG, GoLYTELY® and Nulytely®, which are readily available in most radiology settings. However, lesser or greater amounts of PEG and electrolytes could also be dissolved in a proportional amount of water without departing from the scope of the invention.

In a preferred embodiment, about 100 cc to about 1500 cc of an above described PEG solution is administered to a patient. More preferably, about 250 cc to about 1000 cc of an above described PEG solution is administered to a patient. Amounts of PEG and electrolytes administered to a patient can be based at least in part on the weight of the patient. Generally, patients are given more PEG and electrolytes when their body weight is higher. For instance, a child might receive about 250 cc of PEG and electrolytes, whereas an average-sized adult might receive about 1000 cc of PEG and electrolytes.

In use, where PEG and electrolytes are supplied as a powder, they are resuspended, preferably in water and in the amounts and volumes described above. The PEG and electrolyte mixture is administered to a patient, preferably by having the patient drink it. After about an hour, CT is performed on the patient. Preferably, the CT is of the abdomen and/or pelvis, such that the GI tract can be visualized. It should be understood that although a preferred embodiment of the invention uses CT to produce one or more images, other imaging techniques can also be used with the contrast agents provided herein.

The iso-osmotic contrast agents provided herein can be administered in combination with a positive intravenous "IV" contrast agent, such as an iodine-based contrast agent. The IV contrast agent can be a non-ionic or an ionic contrast agent. IV contrast agents are typically injected into an arm vein. IV contrast agents allow visualization of blood vessels, as well as an improved visualization of such internal organs as the liver, pancreas, kidneys, spleen, and urinary bladder. Administering an oral iso-osmotic contrast agent with a positive IV contrast agent is useful, e.g., in detecting bowel wall enhancement. For this, the IV contrast turns the bowel wall white. The absence of an orally administered positive contrast agent with the iso-osmotic contrast agent improves visualization of the bowel wall because there is no additional illumination within the bowel, which an orally administered contrast agent would disadvantageously provide.

Administering an oral iso-osmotic contrast agent in combination with a positive IV contrast agent is also useful for detecting tumors, inflammation, and ischemia. For instance, inflammatory bowel disease, such as Crohn's disease, can be detected by using an iso-osmotic agent, such as a PEG and electrolytes mixture (hereinafter in this section and in the Examples, when PEG are discussed, it should be understood that the above-mentioned electrolytes are combined with the PEG), and a positive IV contrast. In Crohn's disease, the inflamed bowel wall takes up the IV contrast. The PEG extends the bowel loop such that it can be more easily visualized. Administering PEG without an orally administered positive contrast agent thus permits visualization of the bowel loop because there is no additional illumination within the bowel, which an orally administered positive contrast agent would disadvantageously provide.

Administering oral iso-osmotic contrast agents without an orally administered positive contrast agent can also be used to detect ischemic bowel and tumors of the small bowel. In a preferred embodiment, the oral iso-osmotic agent is administered with a positive IV contrast agent for these applications.

In addition, administering oral iso-osmotic contrast agents without an orally administered positive contrast agent can be of use in detecting partial obstruction of the small bowel. This can be done in combination with a positive IV contrast agent or without such an agent. Partial obstruction of the small bowel preferably is detected by also using a positive IV contrast agent. For instance, when PEG is administered to a patient, it moves through the GI tract via a "wash" of the GI tract. PEG flows downstream due to it being iso-osmotic. On CT, any obstruction in the GI tract of the patient will stand out because the small bowel above the obstruction will be more dilated, whereas the small bowel will be less dilated below the obstruction. The obstruction can therefore be easily identified.

Obstructions of the GI tract can also be visualized using an oral iso-osmotic agent in combination with an oral positive contrast agent. In a preferred embodiment of this technique, PEG is combined with Gastrograffin™ or MD-Gastroview®. The addition of the oral positive contrast agent illuminates the lumen of the GI tract, which can improve visualization of at least some GI tract obstructions.

Using an oral iso-osmotic agent in combination with an oral positive contrast agent was found to consistently and rapidly opacify the terminal ileum and cecum in patients suspected of having appendicitis, as is detailed below in Example 2. When PEG is used as the iso-osmotic agent, the PEG moves rapidly throughout the GI tract, even in the absence of peristalsis.

Another potential use of orally administered iso-osmotic contrast agents, such as PEG, is to negate the need for a nasojejunal tube to facilitate a CT enteroclysis examination for radiologically assessing Crohn's activity. Traditionally, the GI tract is distended by integrating fluid put into it through a nasojejunal tube, which bypasses the stomach. Use of such a tube can be avoided by an orally administered iso-osmotic contrast agent, such as PEG, without an oral positive contrast agent. Such a contrast agent can be used to look for abnormal bowel enhancement of the involved segment of the GI tract in the Crohn's patient. PEG distends the GI tract, especially the small bowel, to a degree that approaches having the GI track distended via a nasojejunal tube, thereby eliminating the need for such a tube.

EXAMPLES

The following Examples are provided for illustrative purposes only. The Example is included herein solely to aid in a more complete understanding of the presently described invention. The Examples do not limit the scope of the invention described or claimed herein in any fashion.

Example 1

This example involves comparing the accepted oral contrast agent for CT angiographic (CTA) techniques (water) with agents that have been used clinically (electrolyte solution and fiber solution) for bowel motility. The utility of these agents compared to the standard of water and dilute iodinated contrast was determined for bowel distension and visualization of bowel wall anatomy/pathology.

Materials and Methods:

In vitro CT exams of the following substances were examined: water, full strength fiber mix, full strength PEG preparation (i.e., PEG with electrolytes), and a mix of full strength fiber and PEG (with electrolytes). Each of these substances were mixed with an artificial flavor that was used to mix the standard dilute iodinated contrast. The dilute iodinated contrast preparation was used as a control because it was previously considered the best contrast agent.

Institutional review board approval was obtained. These materials were offered to outpatients (ranging from 18 to 89 years of age) in random fashion. In each case, the patient was given literature to explain the project and then asked to sign a consent form. Those who declined participation in the study were given dilute iodinated contrast or water as appropriate for the exam. The total numbers of patients enrolled was 98. Out of these, 30 drank water, 32 drank fiber, 11 drank PEG, and 25 drank dilute iodinated contrast. The amount of each material, 1600 cc, and timing, approximately 60 minutes, were standard for the preparation protocol used with dilute iodinated contrast. Although scanning parameters varied slightly, depending on the clinical question, all patients received 5 mm or less slices through the abdomen and pelvis. Only a small minority did not receive intravenous contrast medium, again as clinically indicated. Where given, the intravenous contrast agent was administered from 3-5 cc/sec for 100-150 cc of 300 mg % non-ionic contrast.

Each drink was labeled with a letter A-E to blind the administered substance to the reader. The materials were all near water attenuation except for the dilute iodinated contrast. Each CT scan was read by consensus by two readers. Each exam was rated for various characteristics. The stomach was rated for distention: 1=well distended; 2=adequate distention; 3=poor distention. The small bowel was rated for two characteristics. The distention was assessed with measurements taken from the left upper quadrant (LUQ), the pelvis, and the right lower quadrant (RLQ) areas. Three measures were taken at each area with the greatest diameters used. The diameters were then averaged. The definition of the bowel wall was also graded using visualization of the wall separate from the luminal contents as well as the ability to appreciate the valvulae conniventes when present (1=excellent, 2=good, 3=fair, 4=poor, 5=non-diagnostic). Finally, an attempt was made to assess whether the ingested liquid was able to reach the colon during the preparation time period (0=no oral contrast in colon, 1=oral contrast in colon). This data was evaluated with an ANOVA statistical analysis using the modified LSD (Bonferroni) test with significance level of 0.05.

At exam's end, each patient was given a self addressed stamped envelope with a short survey. The survey asked for an assessment of the drink's taste when compared with the previous standard prep and any untoward effects of the new oral preparation.

Due to initial patient feedback from the PEG group on the follow-up survey and directly to our technical staff, the PEG arm was canceled early and the PEG/fiber portion of the project was not started.

Results:

In vitro CT exams of various liquids were performed to evaluate their respective attenuation values in Hounsfield Units (HU). "Hounsfield Unit" is a unit of x-ray attenuation used for CT scans, each pixel being assigned a value on a scale on which air is −1000, water is 0, and compact bone is +1000. The Hounsfield unit scale can be expanded to up to +3000 and to −3000 units.

FIG. 1A shows an image from an in vitro CT exam that assesses the attenuation value in HU of PEG at full strength (left-hand side of the figure), which had a HU of 5 and PEG at one-half strength (right-hand side of the figure), which had an HU of 3.

Figure 1B:
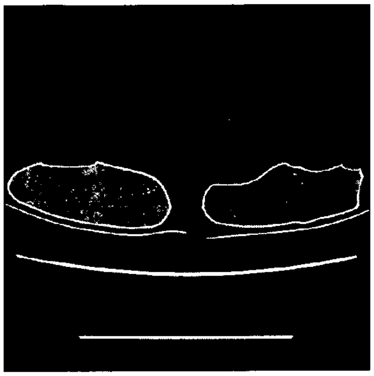

FIG. 1B shows an image from an in vitro CT exam that assesses the attenuation values in HU of 4% milk (left-hand side) (HU 28) and of water (right-hand side) (HU−7).

Figure 1C:
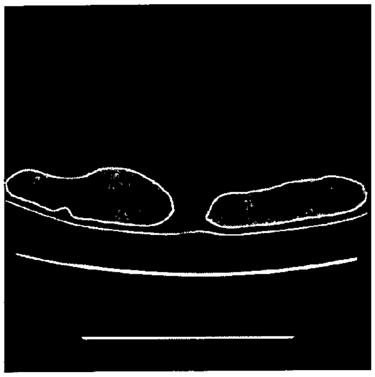

FIG. 1C shows an image from an in vitro CT exam that assesses the attenuation values in HU of fiber at full strength (left-hand side) (HU−1) and of fiber at ½ strength (right-hand side) (HU 1).

Figure 1D:
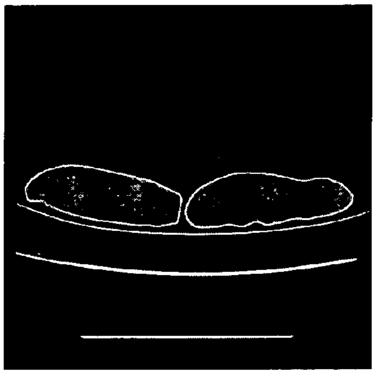

FIG. 1D shows an image from an in vitro CT exam that assesses the attenuation values in HU of methylcellulose (left-hand side) at ½ strength (HU−3) and of methylcellulose at ¼ strength (right-hand side) (HU−11).

Figure 1E:
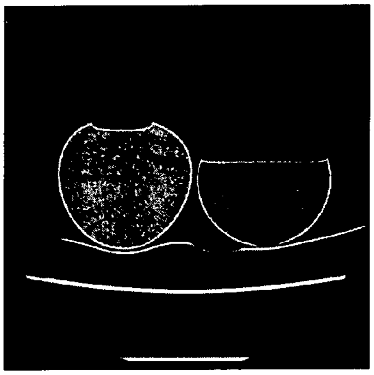

FIG. 1E shows an image from an in vitro CT exam that assesses the attenuation values in HU of $CO_2$ (left-hand side) (HU−3) and of vegetable oil (right-hand side) (HU−127).

Figure 1F:

FIG. 1F shows an image from an in vitro CT exam that assesses the attenuation values in HU of ice cream (left-hand side) (HU−150) and of malt (right-hand side) (-189).

Figure 2A:
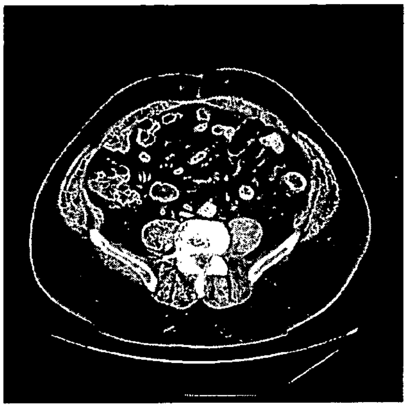
FIGS. 2A-2D show images from CT exams that compare four per oral GI tract agents.
Figure 2B:
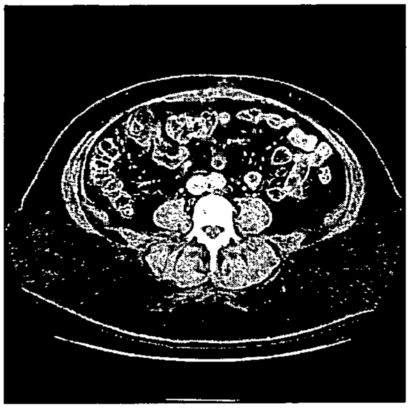
Figure 2C:
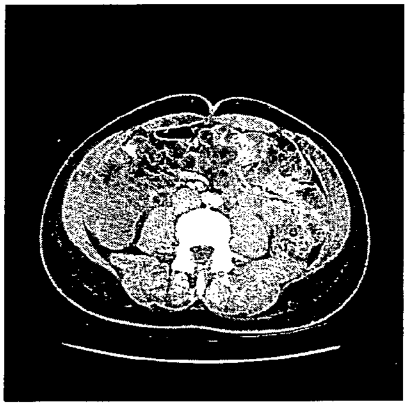
Figure 2D:
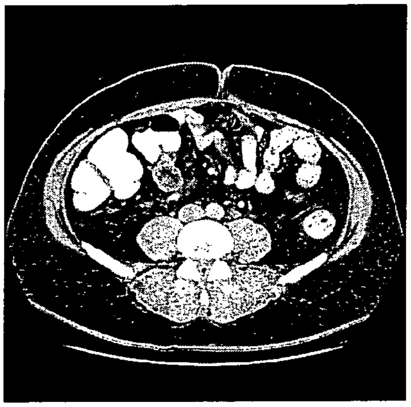

In addition, bowel distension was evaluated. Referring to FIGS. 2A-2D, the following per oral GI tract agents were examined: water (FIG. 2A), fiber (FIG. 2B), PEG (FIG. 2C), and diluted iodinated (FIG. 2D). All patients are different but the slice selection is at the aortic bifurcation. As was true for the study in general, water was the least effective in the mid to distal bowel distention. PEG and dilute iodinated contrast solutions had the best small bowel distention with the agents usually traversing into the colon. Fiber is of intermediate success.

Table 1 below shows gastrointestinal tract distension and visualization results. Several statistically significant differences were demonstrated in both bowel distension and wall visualization. Fiber, PEG, and dilute iodinated contrast all significantly distended the bowel more than water in the LUQ, but the three groups demonstrated no significant difference amongst them. In the pelvis, PEG significantly distended more than both water and fiber, but not dilute iodinated contrast. Dilute iodinated contrast also significantly distended more than water in the pelvis. Although no significant difference in distension is evident in the RLQ, there is a trend with the mean values that is concurrent with the other two areas.

In terms of wall visualization, the only significant difference in qualitative evaluation was improved visualization with PEG compared to fiber. Although there was no significant difference in gastric distension, again seen was a trend for mean values with the best visualization with PEG. Both PEG and dilute iodinated contrast both significantly traversed to the colon more often than water and fiber. There was no statistical difference between PEG and dilute iodinated contrast. Although not statistically significant, the trend for all results was for better distension and visualization with PEG.

TABLE 1

Direct Measurement Comparisons and Qualitative Evaluation of Each Agent

| | # of Patients | LUQ | Pelvis | RLQ | Wall | Stomach | Colon |
|---|---|---|---|---|---|---|---|
| Water | 30 | 17.50 | 14.79 | 14.14 | 2.23 | 2.13 | .020 |
| Fiber | 32 | 20.19 * | 15.67 | 14.86 | 2.30 | 1.88 | 0.39 |
| PEG | 11 | 21.88 * | 18.48 * + | 15.85 | 1.59 + | 1.63 | 1.00 * + |

TABLE 1-continued

Direct Measurement Comparisons and Qualitative Evaluation of Each Agent

| | # of Patients | LUQ | Pelvis | RLQ | Wall | Stomach | Colon |
|---|---|---|---|---|---|---|---|
| Dilute Iodinated | 25 | 20.37 * | 16.87 * | 15.47 | 1.80 | 1.92 | 0.76 * + |

All measurements in millimeters (mm) for LUQ, pelvis, RLQ.
Numbers for wall, stomach, and colon columns indicate qualitative evaluation as described in text.
* Significantly different from water
+ Significantly different from fiber We received fifteen replies out of 43 patients receiving the reply card (patients drinking dilute iodinated contrast and water were not given reply cards due to long experience with these agents). The greatest percentage of responses came from the PEG group with 5 of 11 patients replying but only 10 of 32 fiber patients replying. Four of the PEG responses commented on self-limited loose stools, and two also commented on mild abdominal cramping. Two PEG patients also commented that the PEG taste was worse than on previous CT examinations with dilute iodinated contrast. Only one patient in the fiber group thought the taste was worse than dilute iodinated contrast. The majority commented that the fiber taste was an improvement. Fiber was well tolerated by the majority with only three patients complaining of mild increase in abdominal cramping and gas.

Figure 3A:
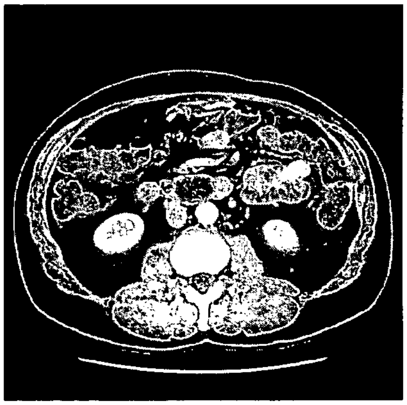
FIGS. 3A and 3B show images from a CT exam that compare PEG preparation with dilute iodinated contrast.
Figure 3B:
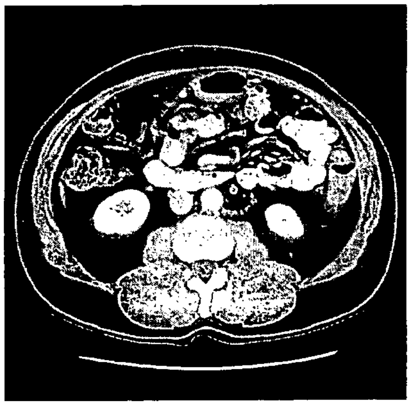

FIGS. 3A and 3B show images from a CT exam that compare PEG preparation with dilute iodinated contrast. A patient serves as his own reference with the present agent, PEG (FIG. 3A), compared with the previous exam obtained with the standard dilute iodinated contrast material (FIG. 3B).

FIGS. 3A and 3B show images from a CT exam that compare PEG preparation with dilute iodinated contrast. A patient serves as his own reference with the present agent, PEG (FIG. 3A), compared with the previous exam obtained with the standard dilute iodinated contrast material (FIG. 3B).

Figure 4:
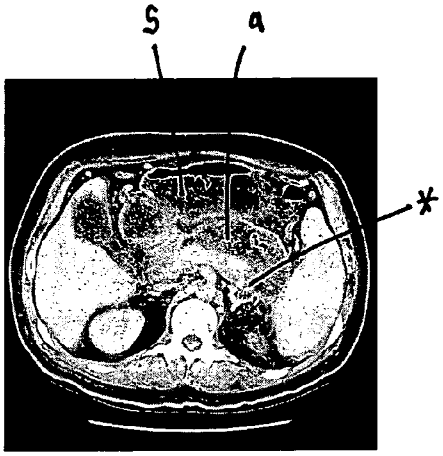
FIG. 4 shows an image from a CT exam that illustrates the difficulty in differentiating abscess from water attenuating bowel agent.

FIG. 4 shows an image from a CT exam that illustrates the difficulty in differentiating abscess from water attenuating bowel agent. In this patient with a pancreatic abscess, it is difficult to distinguish the abscess (denoted as an "a" in FIG. 4) in the pancreatic bed from the fiber filled gastric lumen (denoted as an "s" in FIG. 4) by attenuation alone. The small locules in the area posteriorly (denoted as an "*" in FIG. 4) could also be difficult to separate from a small bowel loop by attenuation.

Figure 5:
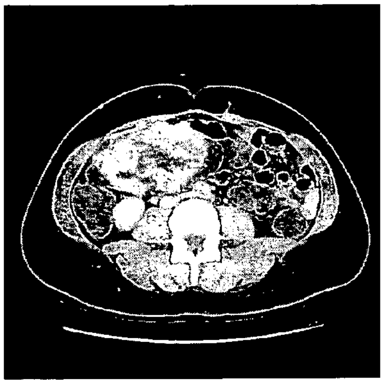
FIG. 5 shows an image from a CT exam that delineates the borders of a high attenuation mass with water attenuating bowel agent.

FIG. 5 shows an image from a CT exam that delineates the borders of a high attenuation mass with water attenuating bowel agent. A 42 year old man with vague abdominal pain has a briskly enhancing, surgically proved, small bowel GIST which is easily separated from the PEG filled small bowel.

Figure 6:
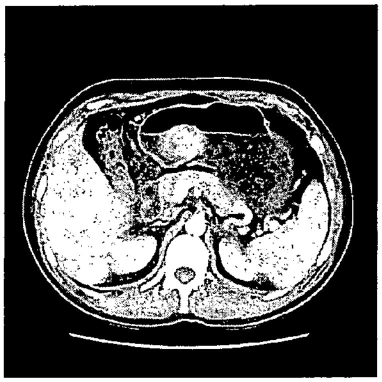
FIG. 6 shows an image from a CT exam that defines a prominently enhancing gastric mass against a water attenuating fluid.

FIG. 6 shows an image from a CT exam that defines a prominently enhancing gastric mass against a water attenuating fluid. A 32-year-old man presented with GI blood loss. Although this huge mass (found to be a GIST at surgery) would have been seen with any GI tract oral agent, a smaller mass of similar attenuation may have been at least partially cloaked by the standard, dilute iodinated agent.

Figure 7:
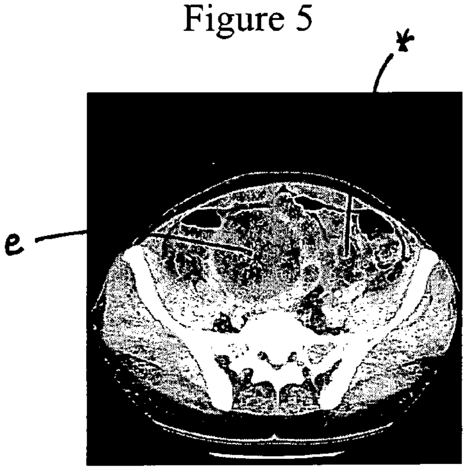
FIG. 7 shows an image from a CT exam illustrating water attenuation small bowel agent adjacent to a pelvic mass.

FIG. 7 shows an image from and a CT exam illustrating water attenuation small bowel agent adjacent to a pelvic mass. This surgically proved endometrioma (denoted as an "e" in FIG. 7) has an attenuation value of 25 HU, just barely perceptibly different than the adjacent PEG filled small bowel loops (denoted as an "*" in FIG. 7), which measure 15 HU.

Discussion:

The recent dramatic advances in CT technology have created many new opportunities in abdominal imaging on the basis of more rapid scanning, thinner sections, and more aggressive contrast enhancement schema. In particular, vascular and parenchymal enhancement, as well as structure display, have dramatically improved. This shift has led us to reconsider the concept of bowel opacification in abdominal/pelvic CT scanning. The presence of high attenuation material in the GI tract may critically hinder obtaining or negate the interpretation of CT angiography (CTA) exams. At our institution, PO, i.e., given by mouth, water is used for bowel distension in all CTA studies. If the patient receives a dilute contrast PO preparation, either by inappropriate physician protocol or by technical error, the subsequent attempted CTA must be canceled. Or worse, if the exam is mistakenly obtained, the image reconstruction is usually nondiagnostic and the exam must be repeated. A universal, low attenuation agent, able to be used for CTA as well as standard imaging of the abdomen and pelvis, would avoid this pitfall.

While water ingestion for CTA has proven adequate for most purposes (5), at times a greater degree of bowel distention is helpful. A frequent example is the importance of duodenal distention in the pancreatic cancer patient undergoing a preoperative CT/CTA.

Gastrointestinal tract distention without high attenuation intraluminal fluid may be helpful in display of bowel pathology. CT is used to assess normal bowel enhancement compared with the under perfused wall in ischemia or the abnormal enhancement in inflammatory bowel assessment. The present multidetector CT protocols allow increased spatial resolution and contrast enhancement of the GI tract, which in turn allows identification of the wall characteristics to identify the normal bowel thus making the traditional high attenuation material unnecessary for this reason alone.

The study's results (Table 1) show that both the PEG preparation and the dilute iodine solution are statistically better for distention of small bowel loops in the left upper quadrant and pelvis, as well as for reaching the colon when compared with the fiber solution and water. The fiber mixture proved also better than water in left upper quadrant small bowel distention. The PEG preparation was shown to be better than fiber and water for small bowel mural characteristic identification with a trend toward improvement over the iodinated agent in this area (FIGS. 3A-3B). Although there was also a trend for the superiority of PEG in the right lower quadrant small bowel distention and gastric distention, this did not reach statistical significance. The lack of statistical significance may be in part related to the smaller number of patients. FIGS. 3A and 3B show the detail of the small bowel wall and the valvulae conniventes and the small bowel distension with the water attenuating, PEG solution. The colon labeled (c) in FIG. 3A is also distended as well. This arm of the project was prematurely ended because of negative patient feedback via the mailing and also the reports from the technical staff that interfaced with this patient population during the exam. Patients appeared to have a strong adverse opinion of the PEG prep compared with the other oral agents because of the subsequent GI complaints and taste. We also cancelled the PEG/fiber preparation portion of the study for the same reason. We will need to reassess the PEG preparation's dosage with further study.

For this study we did not change the oral preparation agent from the standard dilute iodinated agent for inpatients where the possibility of viscus perforation or abscess was higher than that of the outpatient population. We found that for the assessment of bowel perforation, the high attenuation of bowel agent will theoretically be more sensitive. We had no experience of water-attenuation GI tract solution for this clinical question.

We did have cases of abscess formation and tumefaction in patients undergoing water-attenuating GI tract preparations. The delineation of bowel from abscess (FIG. 4) was probably not as obvious as if a high attenuation material had been used, but a distinction was able to be fairly easily made when viewing the entire exam. Depending on the characteristics of the tumefactive process, a high or low attenuation bowel agent would theoretically be advantageous. Lower attenuation neoplasms may be initially more obvious with high attenuation GI tract material. However, the obverse would also be true (FIGS. 5 and 6). As with an abscess, the differentiation of a low attenuation mass with a low attenuation oral agent may not be as obvious initially, but in our case from this study, the difference between bowel and mass was seen (FIG. 7).

Conclusion:

The PEG preparation proved to be competitive with the standard dilute iodinated contrast solution in bowel distention and mural display.

Example 2

Materials and Methods:

Patients: Forty adults needing a CT examination to assist in the work-up of suspected appendicitis were given the oral mixture described below. For comparison, a control group of 40 adults were drawn from review of the medical records where the term "appendix" or "appendicitis" was found in the impression of a radiology CT report. This group was drawn from patients undergoing CT scan as part of the work-up for appendicitis.

Oral Solutions: After trials of various oral solutions for bowel opacification at CT shown in Example 1, PEG was found to have excellent GI tract distention and transit properties. Further studies to define the appropriate attenuation value and amount of PEG-based solution led to the following preparation: 1,000 cc of full-strength PEG solution mixed with 30 cc of water soluble, iodinated contrast agent (MD-Gastroview®, Mallinckrodt Inc., St. Louis, Mo.). This mixture was given in two doses of 500 cc each. The first dose was given at time "0" while a second glass was given at 30 minutes. The patient was then examined at one hour.

The control group received our institution's previous standard preparation which consisted of one glass of 200 cc of water combined with 4 cc of water soluble contrast to be finished within 20 minutes where upon another glass of this solution was given to the patient. A total of eight glasses were given over a 2-2½ hour period after which a CT scan of the abdomen and pelvis was obtained. The patient received a total of 1600 cc of solution having the ratio of 20 cc of iodinated contrast per 1,000 cc of water. Both sets of patients underwent multidetector CT scans of the abdomen and pelvis using 5 mm collimation and reconstruction. Intravenous (IV) contrast was given using 100 cc of nonionic contrast followed by a 50 cc bolus chase of normal saline.

Figure 8A:
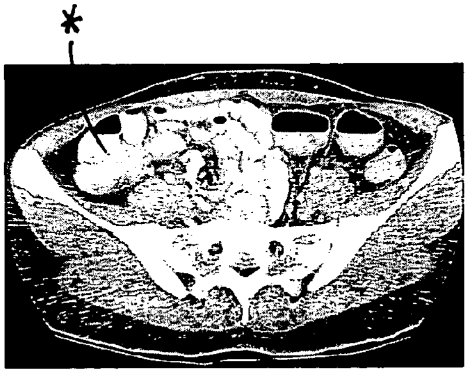
FIGS. 8A-8B show images from CT examinations in a 32 year-old woman (FIG. 8A) and a 45 year-old woman (FIG. 8B) using the PEG/iodine mixture for oral contrast.
Figure 8B:
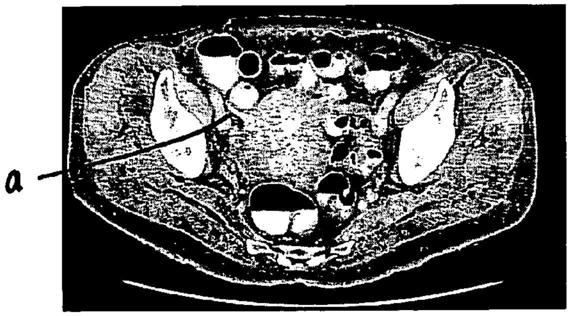

Results:

FIGS. 8A and 8B show images from CT examinations in a 32 year-old woman (FIG. 8A) and a 45 year-old woman (FIG. 8B) using the PEG/iodine mixture for oral contrast. Neither patient had evidence of appendicitis. Notice in FIG. 8A, oral contrast was present in the cecum (denoted with a "*" in FIG. 8A) and filled the appendix (denoted with an "a" in FIG. 8B).

Figure 9:
FIG. 9 shows an image from a coronal reconstructed image from a CT examination in a 17-year-old man with acute appendicitis using the PEG/iodine mixture.

FIG. 9 shows an image from a coronal reconstructed image from a CT examination in a 17-year-old man with acute appendicitis using the PEG/iodine mixture. The oral contrast transited beyond the cecum and extended to an appendicolith (denoted with an arrow in the left lower quadrant of FIG. 9) at the base of the appendix.

Figure 10:
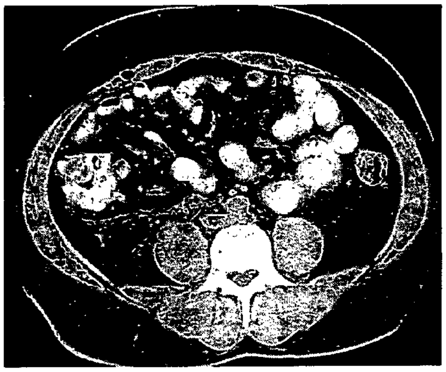
FIG. 10 shows an image from a CT examination in a 45-year-old man with abdominal pain.

FIG. 10 shows an image from a CT examination in a 45-year-old man with abdominal pain. The CT examination demonstrated periureteral inflammatory changes. This patient had a right UVJ calculus. PEG/iodine mixture was identified in the colon even with the adjacent inflammatory process.

Figure 11:
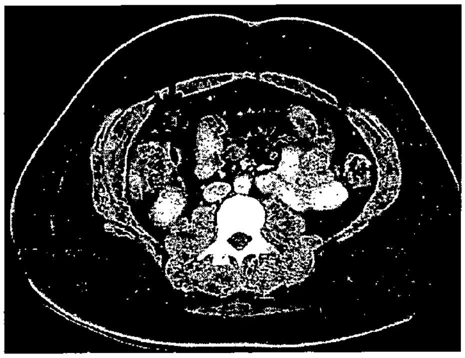
FIG. 11 shows an image from a CT examination in a 28-year-old woman with abdominal pain found to be secondary to epiploic appendagitis (denoted with an arrow in FIG. 11).

FIG. 11 shows an image from a CT examination in a 28-year-old woman with abdominal pain found to be secondary to epiploic appendagitis (denoted with an arrow in FIG. 11). PEG/iodine mixture was used and was found to transit to the colon.

Figure 12:
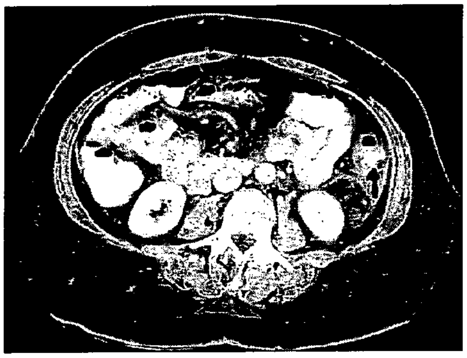
FIG. 12 shows an image from a CT examination in a 56-year-old woman with abdominal pain with PEG/iodine mixture.
Figure 13:
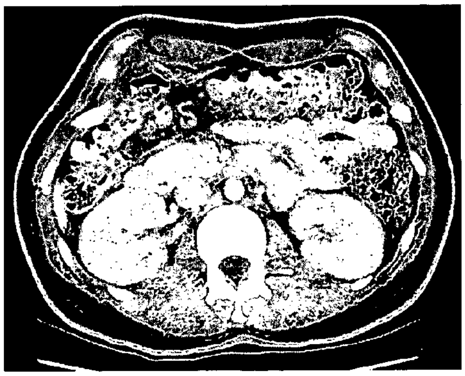
FIG. 13 shows an image from a CT examination in an 18-year-old man with abdominal pain.
Figure 14:
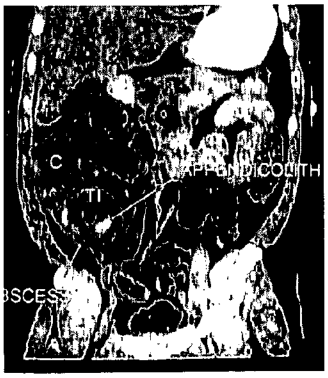
FIG. 14 shows an image from a CT examination in a 44-year-old man with abdominal pain.

FIG. 12 shows an image from a CT examination in a 56-year-old woman with abdominal pain with PEG/iodine mixture. Findings were consistent with diverticulitis (denoted with an arrow in the right-hand side of FIG. 12). Contrast was seen to transit to the colon. The patient was found to have an abnormal enhancement pattern in the kidneys consistent with pyleonephritis. Even with a severe infectious process and a large amount of stool within the colon, the PEG/iodine mixture traversed to the colon. FIG. 14 shows an image from a CT examination in a 44-year-old man with abdominal pain. The patient was found to have small bowel obstruction secondary to periappendiceal abscess. The PEG/iodine mixture did not successfully reach the colon in this patient with inflammatory changes as well as bowel obstruction.

Of the 40 patients given the PEG/iodinated contrast drink, 38 of the 40 patients had contrast at least to the cecum when examined at one hour (see Table 2 below). Twenty of these 40 patients had radiologic evidence and subsequent surgical confirmation of appendicitis. Five other patients had different diagnoses found at CT examination (see Table 3 below). The only two patients whose contrast did not reach the colon both had appendicitis. One had an uncomplicated appendicitis while the second had a complicated, walled off abscess from a perforated appendix (FIG. 14).

TABLE 2

| | Colonic Transit | |
|---|---|---|
| Contrast Agent | +Colon | −Colon |
| PEG/Iodinated Contrast | 38 | 2 |
| Water/Iodinated Contrast | 18 | 22 |
| (Fisher exact test p value <0.0001) | | |

TABLE 3

| Contrast Agent | Patient Diagnosis +Appendicitis | Other |
|---|---|---|
| PEG/Iodinated Contrast | 20 | 2 - Left sided Diverticulitis<br>1 - Right UVJ Stone<br>1 - Bilateral Pyelonephritis<br>1 - Right Sided Epiploic Appendagitis |
| Water/Iodinated Contrast | 11 | 1 - Left Sided Diverticulitis<br>1 - Right UVJ Stone<br>1 - Crohn's Disease of TI<br>1 - Pancreatitis |

Only 18 of 40 patients in the control group had contrast within the colon after a 2-2½ hour preparation time with 1600 cc of the standard mixture (see Table 2). Eleven patients in this group had radiologic and surgical confirmation of appendicitis. Seven of these eleven patients had contrast traversing to the colon during the preparation time. Within the remaining group of 29 non-appendicitis patients, four had another diagnosis for the cause of abdominal pain (see Table 3). Of this latter group, only the patient with pancreatitis had contrast travel to the colon.

Although not the focus of this work, there were four false/positive CT exams. Three of the four were seen in the standard oral contrast group. In this group, two of the cases did not have contrast into the colon. However, when reviewing these cases, the presence or absence of colonic contrast did not play a role in interpretation.

Discussion:

Consensus has not been reached on preparation of the patient suspected of appendicitis undergoing CT examination. CT exams are done without any contrast given to a variety of combinations of oral, IV, and/or rectal contrast. We found that, especially in the thin patient without fat helping define the periappendiceal area, GI tract contrast in the terminal ileum and cecum, as well as IV contrast, are very important. In an attempt to opacify the terminal ileum and cecum in our ER population prior to CT, we increased the drink time to 2 to 2½ hours and gave the patient 1600 cc of our standard dilute water soluble contrast which was mixed in a ratio of 20 cc of iodinated contrast per 1000 cc of water. Even with this protocol, the desired opacification was still unreliable and the emergency room personnel continued to be frustrated with the turn around time for their patients.

From our research shown in Example 1 we had found that the full-strength PEG solution could provide excellent GI tract distention and reliable transit time to the colon. Subsequently we made modification to this solution through further studies and found that 1000 cc of PEG mixed with 30 cc of full strength water soluble contrast agent gave excellent GI tract distention with very reliable transit time as well as good luminal opacification in the general abdomen/pelvic CT patient. It seemed reasonable to study this mixture in the patient population with a possible inflammatory process such as appendicitis.

The formulation used to create the PEG solution causes a transition of fluid in the GI tract as a "wash" and is less dependent on the stimulation of bowel contraction that is used to move the fluid with the dilute water soluble contrast agent. The presence of peritonitis from an abdominal inflammatory process such as appendicitis could theoretically cause a reflux ileus and therefore negate the contractions from the water soluble contrast. The ability to "wash" fluid down the GI tract without a dominant component of contraction would make the PEG solution more effective in this circumstance (FIG. 9). However, the addition of the water-soluble contrast agent to the PEG solution in order to help luminal opacification probably contributes to propagation of this mixture through the GI tract.

The present study shows a marked improvement of the PEG/iodine solution over the same iodinated contrast solution diluted with water. The patient has to ingest significantly less fluid with the PEG solution, 1000 cc versus 1600 cc, and wait half as long before his/her exam. Whereas only 18 of 40 patients ingesting the standard oral mixture had contrast reached the colon in 2 to 2½ hours, 38 of 40 patients had contrast to the colon at one hour in the PEG group.

One of the two patients who did not have contrast to the colon in the PEG group had an uncomplicated appendicitis. We are not sure what caused this delay. The second case, however, had a complicated, probably subacute perforated appendix with abscess formation. There were adhesions to the terminal ileum as this segment of bowel was recruited to wall off the abscess that had occurred (FIG. 14). Therefore, when the combination of peritonitis and obstruction is present, it appears that even the PEG solution will not be effective.

However, 18 of the 20 patients with surgically proved appendicitis did have contrast transit to the colon. There were five other significant findings on CT in this group (see Table 2) and the PEG solution was able to reach the colon with these intraabdominal processes as well (see FIGS. 10-13).

Conclusion:

The oral contrast solution of 1000 cc of PEG mixed with 30 cc of iodinated contrast agent provides a relatively rapid and very dependable opacification of the GI tract including the terminal ileum and colon even in the face of appendicitis.

It is understood that the various preferred embodiments are shown and described above to illustrate different possible features of the invention and the varying ways in which these features may be combined. Apart from combining the different features of the above embodiments in varying ways, other modifications are also considered to be within the scope of the invention.

BIBLIOGRAPHY

1. Malik N, Khandelwal N, Garg K, Suri S. Computed tomography of the abdomen with fat density oral contrast medium. Australas Radiol 1992; 36:31-33.
2. Raptopoulos V, Davis M A, Davidoff A, et al. Fat-density oral contrast agent for abdominal CT. Radiology 1987; 164:653-656.
3. Spilde J, Lee F L, Chosy S, et al. Evaluation of an experimental low-attenuation gastrointestinal contrast agent for CT imaging of intestinal ischemia in an animal model. Acad Radiol 1999; 6:94-101.
4. Thompson S, Raptopoulos V, Shieman R, et al. Abdominal helical CT: milk as a low-attenuation oral contrast agent. Radiology 1999; 211:870-875.
5. Winter T C, Ager J D, Nghiem H V, Hill R S, Harrison S D, Freeny P C. Upper gastrointestinal tract and abdomen: water as an orally administered contrast agent for helical CT. Radiology 1996; 201:365-370.
6. Zwaan M, Gmelin E, Borgis K J, Rinast E. Non-absorbable fat-dense oral contrast agent for abdominal computed tomography. Eur J Radiol 1992; 14:189-191.

What is claimed is:

1. A method of imaging a portion of a body of a patient, the method comprising:

(A) administering (i) about 100 cc to about 1500 cc of an iso-osmotic agent and (ii) a positive contrast agent to the patient, wherein the iso-osmotic agent administered to the patient comprises a mixture of polyethylene glycol and electrolytes, and wherein the positive contrast agent is selected from the group consisting of an iodine-based contrast agent and a barium-based contrast agent;

(B) distending at least the small bowel of the patient with the iso-osmotic agent and the positive contrast agent; and (C) obtaining a plurality of successive images by computed tomography of at least one of the small bowel and the cecum of the patient body after the iso-osmotic agent and the positive contrast agent are administered and while the small bowel is distended throughout substantially its entirety by the iso-osmotic agent and the positive contrast agent, wherein the positive contrast agent improves the obtained images.

2. The method of claim 1, wherein the obtaining step comprises obtaining a plurality of successive images of the appendix of the patient, and further comprising determining whether the patient has appendicitis.

3. The method of claim 1, wherein the polyethylene glycol administered to the patient comprises about 65 g to about 500 g of polyethylene glycol dissolved in about 4000 cc of liquid.

4. The method of claim 3, wherein the polyethylene glycol administered to the patient comprises about 236 g to about 420 g of polyethylene glycol dissolved in about 4000 cc of liquid.

5. The method of claim 1, wherein about 250 cc to about 1000 cc of the iso-osmotic agent is administered to the patient.

6. The method of claim 1, further comprising intravenously administering a positive IV contrast agent to the patient.

7. The method of claim 6, wherein the positive IV contrast agent comprises an iodine-based contrast agent.

8. The method of claim 1, wherein the obtaining step is performed about an hour after the administering step.

9. The method of claim 1, further comprising detecting partial obstruction of the small bowel of the patient.

10. The method of claim 6, further comprising visualizing the bowel wall of the patient.

11. The method of claim 1, further comprising detecting a tumor, inflammation, or ischemia in the patient.

12. A method of imaging a portion of a body of a patient, the method comprising:

(A) administering (i) about 100 cc to about 1500 cc of an iso-osmotic agent and (ii) a positive contrast agent to the patient, wherein the iso-osmotic agent administered to the patient comprises a mixture of polyethylene glycol and electrolytes, and wherein the positive contrast agent is selected from the group consisting of an iodine-based contrast agent and a barium-based contrast agent;

(B) distending at least the small bowel of the patient with the iso-osmotic agent and the positive contrast;

(C) administering a positive contrast agent intravenously to the patient; and (D) obtaining a plurality of successive images by computed tomography of the portion of the patient's body after the iso-osmotic agent and the positive contrast agent are administered and while the small bowel is distended throughout substantially its entirety by the iso-osmotic agent and the positive contrast agent, wherein the positive contrast agent improves the obtained images.

13. The method of claim 12, wherein the positive contrast agent comprises an iodine-based contrast agent.

14. The method of claim 1, wherein the polyethylene glycol administered to the patient comprises about 32.5 g to about 250 g of polyethylene glycol dissolved in about 4000 cc of liquid.

15. The method of claim 12, wherein the polyethylene glycol administered to the patient is mixed at a ratio of about 65 g to about 500 g of polyethylene glycol and about 4000 cc of liquid.

16. The method of claim 12, wherein the polyethylene glycol administered to the patient is mixed at a ratio of about 32.5 g to about 250 g of polyethylene glycol and about 4000 cc of liquid.

* * * * *

UNITED STATES PATENT AND TRADEMARK OFFICE

CERTIFICATE OF CORRECTION

PATENT NO. : 7,582,283 B2
APPLICATION NO. : 10/794043
DATED : September 1, 2009
INVENTOR(S) : Taylor et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1384 days.

Signed and Sealed this

Fourteenth Day of September, 2010

David J. Kappos
*Director of the United States Patent and Trademark Office*